US008066881B2

(12) United States Patent
De Magalhães Nunes Da Ponte et al.

(10) Patent No.: US 8,066,881 B2
(45) Date of Patent: Nov. 29, 2011

(54) METHOD OF OBTAINING A NATURAL HYDROXYTYROSOL-RICH CONCENTRATE FROM OLIVE TREE RESIDUES AND SUBPRODUCTS USING CLEAN TECHNOLOGIES

(76) Inventors: Manuel Luís De Magalhães Nunes Da Ponte, Cruz Quebrada (PT); José Luís Cardador Dos Santos, Almada (PT); Ana Alexandra Figueiredo Matias, Charneca da Caparica (PT); Ana Vital Morgado Marques Nunes, Lisboa (PT); Catarina Maria Martins Duarte, Setúbal (PT); João Paulo Serejo Goulão Crespo, Lisboa (PT)

( * ) Notice: Subject to any disclaimer, the term of this patent is extended or adjusted under 35 U.S.C. 154(b) by 0 days.

(21) Appl. No.: 12/020,960

(22) Filed: Jan. 28, 2008

(65) Prior Publication Data

US 2008/0179246 A1    Jul. 31, 2008

Related U.S. Application Data

(63) Continuation of application No. PCT/IB2006/052552, filed on Jul. 25, 2006.

(30) Foreign Application Priority Data

Jul. 27, 2005   (PT) .......................................... 103326

(51) Int. Cl.
*A61K 36/63*   (2006.01)
*A61K 36/00*   (2006.01)
*C02F 1/44*    (2006.01)

(52) U.S. Cl. ........................ 210/637; 210/652; 424/725

(58) Field of Classification Search .................. None
See application file for complete search history.

(56) References Cited

U.S. PATENT DOCUMENTS

2003/0108651 A1 * 6/2003 Crea .............................. 426/615

FOREIGN PATENT DOCUMENTS

| EP | 1623960 A1 | | 2/2006 |
| ES | 2007230 A | * | 6/1989 |
| WO | 02/18310 A1 | | 3/2002 |

OTHER PUBLICATIONS

Allouche et al., Phenolic compounds with antioxidant activity from olive mill wastewaters, Journal de la Societe Chimique de Tunisie (2004), 6 (1), 33-43.*

Chan et al, Preparation and characterization of nanofiltration membranes fabricated from poly (amidesulfonamide), and their application in water-oil separation (Journal of applied polymer science, 87: 1803-1810, 2003.*

Skaltsounis, L., et al., "Minos Project Process development for an integrated olive mill waste management recovering natural antioxidants and producing organic fertilizer," Internet Citation [Online] Apr. 2004, Retrieved from the Internet: URL:http://www.pharm.uoa.gr/minos/manualeng.pdf> [retrieved on Nov. 16, 2005].

* cited by examiner

*Primary Examiner* — Qiuwen Mi
(74) *Attorney, Agent, or Firm* — Sughrue Mion, PLLC

(57) ABSTRACT

A process of obtaining a natural, bioactive concentrate, rich on hydroxytyrosol, from olive tree residues and subproducts using clean technologies is presented. These technologies comprise supercritical fluid extraction, nanofiltration and reverse osmosis which are used individually or in an integrated mode. The natural extract comprises hydroxytyrosol at a minimum concentration of 15% (mass fraction) and a maximum concentration of 98% (mass fraction). The hydroxytyrosol-rich concentrate exhibits anti-oxidant, anti-microbial, anti-inflammatory and anti-carcinogenic activities, which are superior to the activities observed for isolated hydroxytyrosol in equivalent concentration. The hydroxytyrosol-rich concentrate can be prepared in the form of solid particles, as an aqueous solution, in an emulsion or as lipidic based nanoparticles. Industrial application includes the food, pharmaceutical and cosmetics industries.

20 Claims, 6 Drawing Sheets

METHOD OF OBTAINING A NATURAL HYDROXYTYROSOL-RICH CONCENTRATE FROM OLIVE TREE RESIDUES AND SUBPRODUCTS USING CLEAN TECHNOLOGIES

OBJECT AND FIELD OF THE INVENTION

The present invention relates to a process of obtaining a natural, bioactive concentrate, from olive tree residues and subproducts using clean technologies. These technologies comprise supercritical fluid extraction, nanofiltration and reverse osmosis. Particularly, the invention provides an olive extract containing hydroxytyrosol, and a method of obtaining the same.

The hydroxytyrosol-rich concentrate has an important added value as anti-oxidant, anti-microbial, anti-inflammatory and anti-carcinogenic. Industrial application comprises the food, pharmaceutical and cosmetics industries.

BACKGROUND OF THE INVENTION

Over the last years, several epidemic studies have been correlating the Mediterranean diet with the low frequency of heart diseases, atherosclerosis and defined types of cancer. A particular characteristic of the Mediterranean diet is the use of olive oil, directly consumed or used for cooking (Visioli et al., 2002; Owen et al., 2000).

Studies concerning biophenolic compounds present in olives and olive leafs, draw researchers to recognize their biological properties, which were also associated with the positive health properties of olive oil. Therefore, the bioactive compounds present in olives and olive oil were recognized as important targets for the pharmaceutical and the food industry (Schieber et al., 2001). However, 98% of these biophenolic compounds are lost during olive oil production and remain in vegetation water and/or solid residues resulting from olive processing (Rodis et al., 2002).

The compounds present in higher concentrations in the solid residues are glycosylated secoiridoids, while in vegetation water the compounds with higher concentration are secoiridoids derivatives, mostly hydroxytyrosol and oleoeuropein (Mullinacci et al., 2001).

The properties of the solid residues obtained during olive oil production, as well as extracts obtained from them, have been studied (Visioli et al., 1999); in particular, their antibacterial activity has been shown (Ramos-Cormenzana et al., 1996), and associated with the presence of oleoeuropein and hydroxytyrosol; this last compound was referred to be the compound with a higher bio-activity (Bisignano et al., 1999).

Hydroxytyrosol has been also referred as a potent chemopreventive agent (Manna et al., 2000), and considered as the component present in olive oil residues with higher anti-oxidant potency. The first recognized properties of hydroxytyrosol were its ability to prevent the oxidation of the low density lipoprotein (LDL) (Visioli and Galli, 1998) and the aggregation of blood platelet (Petroni et al., 1995). Mana et al. (2000) proved that this compound is able to protect several cellular human systems from the toxicity induced by reactive oxygen species. The ability of hydroxytyrosol to induce DNA modifications has been also investigated (Aruoma et al., 1999 and Deima et al., 1999).

Visioli et al. (2000) has also shown that, depending on the dosage, this biophenolic compound is well absorbed by humans, being excreted in urine as glucuronate conjugates.

Nowadays, olive oil is exclusively produced by using mechanical and physical methods, that consist on pressing the fruit (pulp and stones) until obtaining a homogeneous slurry, which is then processed for phase separation.

The traditional phase separation step uses hydraulic presses, which have been replaced by continuous centrifugation. The continuous process is also named three-phase process, when olive oil, vegetation water and olive cake are obtained as final products, or as two-phase process when the final product streams are olive oil and olive cake.

In the three-phase system, it is added water to the olive slurry and this mixture is then processed by a horizontal centrifuge, where the solid phase is separated from the oily must. This must is then processed by a vertical centrifuge, where the olive oil is separated from the vegetation water.

The most common method, nowadays, is the two-phase method because it involves a lower consumption of water. Consequently it produces a lower amount of residual water. This process uses two-phase centrifuges that separate olive oil and olive cake. The olive cake is a semi-solid residue with a slurry-type aspect.

Several patents have been published, which present methods for the recovery of fenolic compounds from olive tree residues. The U.S. Pat. No. 6,361,803 describes a method for the recovery of antioxidant compounds from olive residues. This method consists on a preliminary extraction with an aqueous solvent, being the extract produced fed to an adsorption column, in order to retain the compounds of interest. These compounds are recovered subsequently by eluting an organic solvent through the adsorption column. The U.S. Pat. No. 6,849,770 describes a method for the recovery of hydroxytyrosol by a chromatographic method using methanol or water/ethanol mixtures as elution solvents.

The WO0218310 describes a method of obtaining a hydroxytyrosol-rich composition from vegetation water using a previously patented method (U.S. Pat. No. 5,490,884), known as Porocrit. Extraction of the target compounds from vegetation water is achieved using supercritical fluids, such as carbon dioxide, and porous membranes instead of contacting columns. Instead of dispersing the phases, the liquid is fed continuously through porous polypropylene membranes configured as hollow fibre bundles or spiral wound sheets. The liquid passes through the porous membranes within a pressurized module, while supercritical carbon dioxide flows counter-currently on the other side of the membrane. It is important to notice, according to the authors of this patent, that the pressure in the module is essentially the same, so that the extraction is driven by the concentration gradient between the fluid and the supercritical carbon dioxide and not by a pressure gradient between the two sides of the membrane. The extract may be recovered by vaporizing the carbon dioxide for recycling. Additionally, the U.S. Pat. No. 5,714,150 describes a method for extraction of oleuropein from leafs of the olive tree by using water/ethanol mixtures.

The use of membrane filtration methods and their integration with other techniques, such as centrifugation, have been reported by research groups aiming to develop processes for treatment of olive mill wastewaters.

The WO0218310 disclosed process differs from the one of the present invention mainly because it does not include a reverse osmosis operation being this operation comprised in the second step of the present invention. Other differential aspect of this process is that the pressure in the two opposite sides of the membrane is essentially the same, so that the extraction is driven by the concentration gradient between the fluid and the supercritical carbon dioxide and not by a pressure gradient between the two sides of the membrane. Consequently, the product obtained by the process described in of WO0218310 is substantially different from the extract obtained according to the process of the present invention, which, most preferentially, excludes compounds with a molecular weight above 300 Da.

Drouiche et al. (2004) describe the use of ultrafiltration to remove the particles and organic compounds from vegetation water. The work published by Turano et al. (2002) describes a process which integrates centrifugation and ultrafiltration for treatment of vegetation water. In this integrated process, centrifugation allows to remove the suspended solids fraction protecting the ultrafiltration membrane from severe fouling problems caused by these particulates.

DellaGreca et al. (2001 and 2004) report an analytical method developed for characterization of vegetation water. This method involves the fractionation of vegetation water in order to obtain isolated, individual components, present in the water. A series of membrane techniques is used for this purpose.

Document US 2003/0108651 refers to a process different from the one described in the present invention, namely because it does not include a reverse osmosis operation, which is comprised in the second step of the present invention. As a consequence of using different processes, the complex extract obtained according to the process of the present invention is different from the product obtained by the process described in US 2003/0108651, which describes that the method comprises fractionating the incubated vegetation water to separate hydroxytyrosol from other components. Additionally, this method uses for fractionation and separation of hydroxytyrosol the incubation of vegetation water with an organic solvent, namely ethyl acetate, and further comprises the purification of hydroxytyrosol by chromatography. Contrarily, the present invention does not comprise the separation of hydroxytyrosol nor its purification by chromatography or by any other means once it aims to obtain a biological extract, which comprises hydroxytyrosol and other bioactive compounds.

EP 1 623 960 A1 describes a process for the treatment of oil mill wastewaters allowing for the recovery of highly pure tyrosol and hydroxytyrosol. In order to obtain such product, this process uses membrane techniques. Additionally, the compound tyrosol recovered from oil mill wastewaters is catalytically converted to hydroxytyrosol. Therefore, this process aims for obtaining highly pure compounds instead of natural complex extracts from olive oil sub-products.

Skaltsounis, L. et al. (MINOS PROJECT Process development for an integrated olive mill waste management recovering natural antioxidants and producing organic fertilizer) describes an adsorption process, since it uses a resin to capture polyphenols from olive mill wastewaters. The polyphenols captured in the resin medium are therefore recovered by using an organic solvent. Further, these polyphenols are thermally recovered from the organic solvent used and separated by chromatography. Nanofiltration/reverse osmosis are referred in this project as a way to treat the resin brine outflow effluent, which is rich in mineral salts (counter-ions from the resin material) but does not contain polyphenols. Thus, the above mentioned process is totally different from the one described in the present invention due to the use of that resin to isolate the olive mill wastewaters polyphenols instead of using a two-step process consisting in extracting the biological compounds by means of a supercritical fluid extraction column or a nanofiltration unit, and then using a reverse osmosis unit to obtain a biological extract containing hydroxytyrosol.

A process using clean technologies able to recover, from olive oil residues, a complex, natural extract, rich in hydroxytyrosol and containing other bioactive compounds with desirable properties, while assuring the rejection of compounds with higher molecular weight and detrimental biological properties is not available.

Hydroxytyrosol rich concentrates are available in the market as a dietetic supplement. One of these products is produced according with the patented process WO 0218310 previously referred. It is claimed that this concentrate can be used as a natural anti-bacterial, anti-viral and/or anti-fungi agent in agriculture, as well as a therapeutical agent or food additive.

In fact, studies were carried-out in order to compare the result of the process disclosed in document WO0218310, a commercial product designated as Hydrox®, Creagi, and the extract obtained by the process of the present invention. Both products were tested for the cytotoxicity on CACO-2 (human colon) cell line and anti-proliferative activity on HT-29 (human colon cancer cell line. Results show that both extracts are not cytotoxic for the CACO-2 (human colon) cell line. However, the proliferative inhibitory effect of the natural extract produced by the present invention, on the tested human cancer cell line, is higher (110% higher for concentrations of polyphenols above 200 mg/L) than the biological activity exhibited by the product obtained according to the process described in WO0218310.

Furthermore the present invention uses as feedstock any type of olive tree residue including solid residues and does not aim at the isolation of hydroxytyrosol by itself, but at obtaining a complex extract rich in this compound comprising also other bioactive compounds.

BRIEF DESCRIPTION OF THE INVENTION

The present invention relates to a process of obtaining a natural, bioactive concentrate, rich on hydroxytyrosol, from olive tree residues and subproducts using clean technologies, comprising one of the following steps: (a) supplying a flow stream containing hydroxytyrosol and other bioactive compounds from the olive tree to a supercritical fluid extraction column where the said hydroxytyrosol and bioactive compounds are recovered to an extract stream, or (b) supplying a flow stream containing hydroxytyrosol and other bioactive compounds from the olive tree to a nanofiltration unit where the said hydroxytyrosol and other bioactive compounds are recovered in the permeate stream of said nanofiltration, which are followed by step (c) that consists of supplying the extract stream of said supercritical fluid extraction column or the permeate stream of said nanofiltration operation to the feed compartment of a reverse osmosis unit where the said hydroxytyrosol and bioactive compounds are retained and concentrated in the retentate stream.

The natural extract comprises a minimum concentration of 15% (mass fraction) in hydroxytirosol and a maximum concentration of 98% (mass fraction) in this compound. The hydroxytyrosol-rich concentrate exhibits anti-oxidant, anti-microbial, anti-inflammatory and anti-carcinogenic activities, which are superior to the activities observed for isolated hydroxytyrosol, in equivalent concentration. The hydroxytyrosol-rich concentrate can be prepared in the form of solid particles, as an aqueous solution, in an emulsion or as lipidic based nanoparticles. Industrial application comprises the food, pharmaceutical and cosmetics industries.

BRIEF DESCRIPTION OF THE DRAWINGS

To complement this description and with the object of helping towards a better understanding of the characteristics of the invention, a detailed description of a preferred embodi

DETAILED DESCRIPTION OF THE INVENTION

Figure 1:
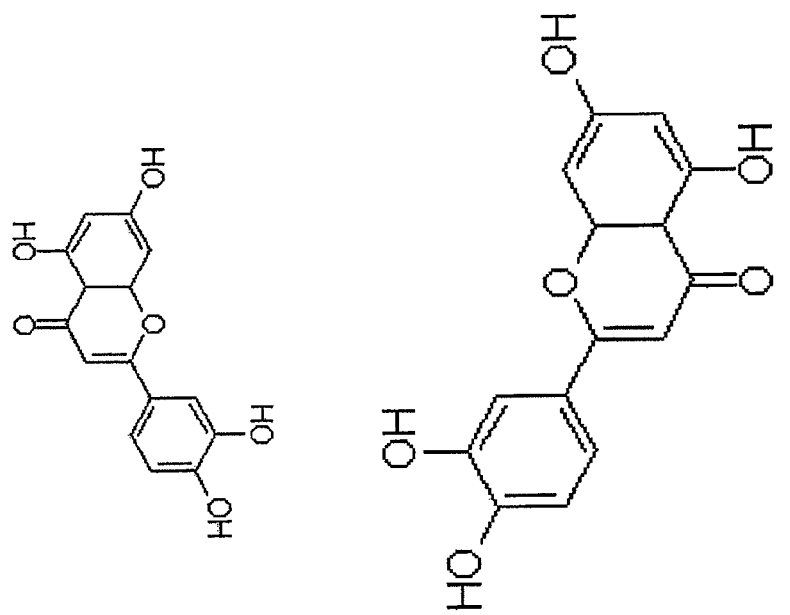
- FIG. 1 shows the chemical structure of some of the phenolic compounds present in the two-phase residues.
Figure 1:
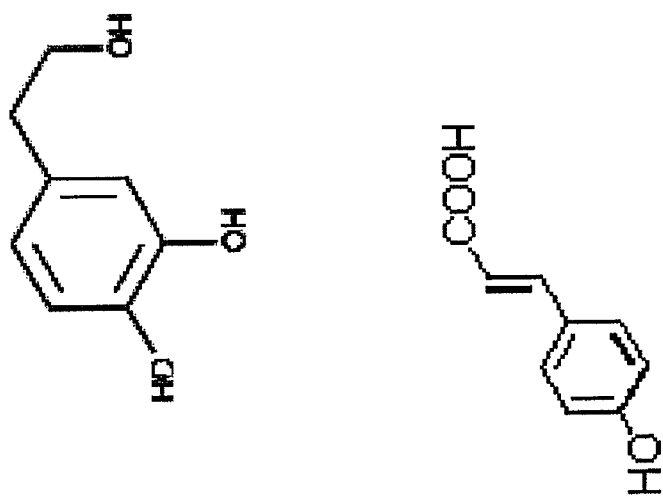

The present invention relates to a process of obtaining a natural, bioactive concentrate, rich on hydroxytyrosol, from olive tree residues and subproducts using clean technologies. These technologies comprise supercritical fluid extraction, nanofiltration and reverse osmosis which are used individually or in an integrated mode. By using this process one or more bioactive solutes present in the olive tree residues and subproducts are recovered in the extract. The chemical structures of some of these compounds are shown in FIG. 1.

The olive tree residues and subproducts include: i) vegetation waters and solid residues from olive mills that operate according to the three-phase process; ii) semi-solid residues from olive-mills that operate according to the two-phase process; iii) olive stones and olive leafs.

Figure 2:
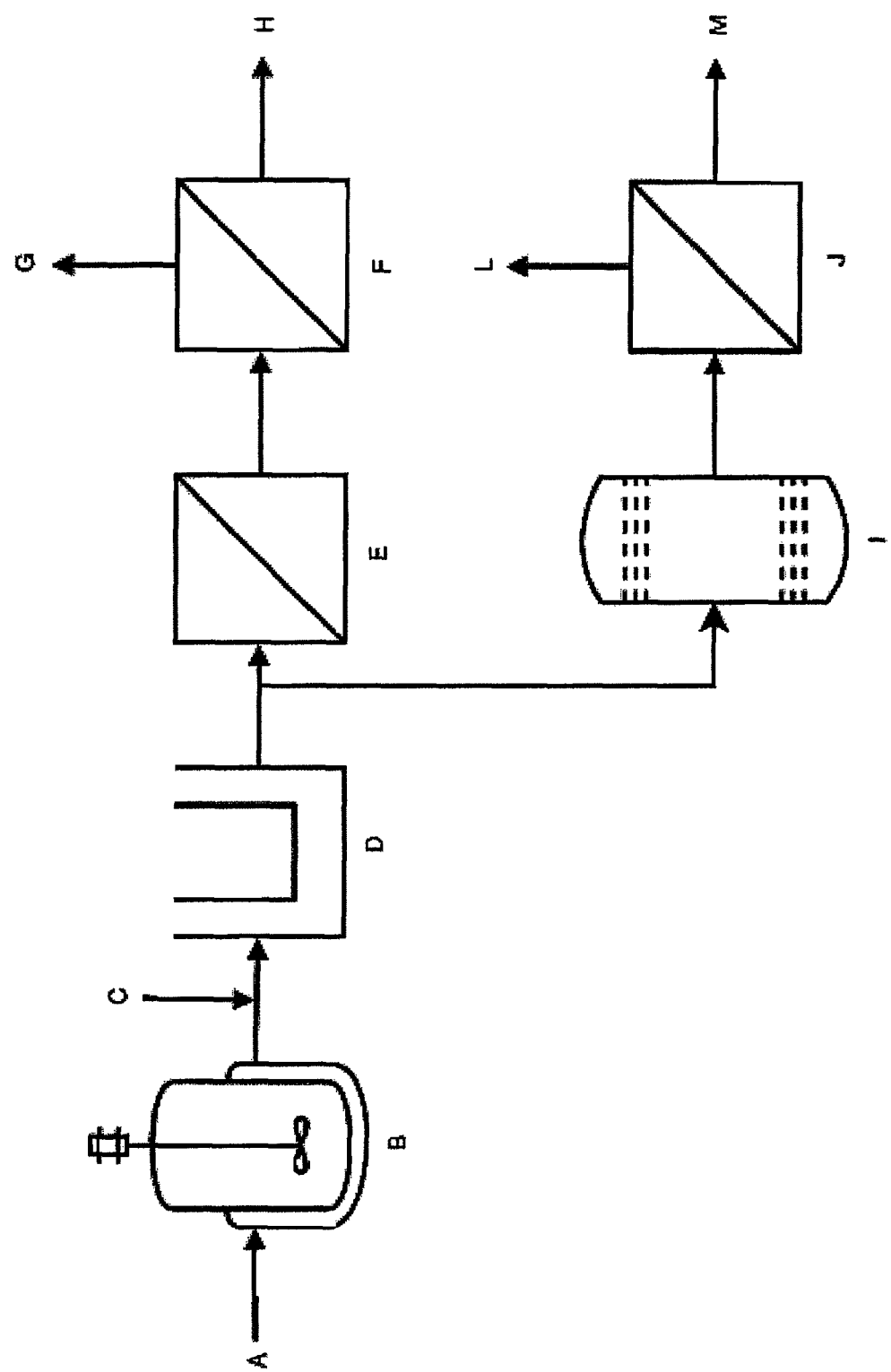
FIG. 2 shows a schematic diagram of the integrated process, which has been used in the embodiment of the process object of the present invention.

FIG. 2 shows a schematic diagram of the integrated process, which has been used in the embodiment of the process object of the present invention. This figure comprises the following operations: extraction with biocompatible solvents, selective recovery of bioactive solute(s) by using supercritical fluid extraction, or nanofiltration, and reverse osmosis. The first step consists on the processing of solid and semi-solid residues from the olive tree (A) by extraction with water or other biocompatible solvents (B), such as hydroalcoholic mixtures. The resulting extract may be fed directly to the supercritical fluid extraction unit (I) or to the nanofiltration unit (E), or alternatively, it may be mixed with vegetation waters from olive mills and centrifuged (D) in order to remove particles and other suspended solids. In this later case, the supernatant of the centrifuge is fed to the supercritical fluid extraction unit (I) or to the nanofiltration unit (E). The nanofiltration operation separates hydroxytyrosol and other bioactive compounds with low molecular weight compounds, which are recovered in the permeate stream produced, from compounds with higher molecular weight which are retained in the retentate stream. In order to increase the concentration of hydroxytyrosol and the other bioactive compounds present in the permeate, this stream may be fed to a reverse osmosis unit (F). This operation produces a retentate stream rich in hydroxytyrosol and the other bioactive compounds of interest (G) and an aqueous stream (H) which may be reused in the extraction step (B) or disposed in the environment. The supercritical extraction process comprises a supercritical extraction column (I), where hydroxytyrosol and other bioactive compounds are recovered, and separated from other components of the feed. The stream rich on hydroxytyrosol and other bioactive compounds may then be fed to a reverse osmosis unit (J) in order to increase their concentration. This operation produces a retentate stream rich in hydroxytyrosol and the other bioactive compounds of interest (L) and an aqueous stream (M) which may be reused in the extraction step (B) or disposed in the environment.

In order to design a process that allows for an effective recovery of the bioactive compounds of interest, with high yields and high selectivity, it is necessary to define the optimal conditions for integration of the different steps involved. This integration involves the selection of an adequate and biocompatible solvent for extraction, and the selection of the operating conditions of the supercritical fluid extraction unit and the nanofiltration and reverse osmosis steps.

Supercritical fluids are gases at ambient temperature and atmospheric pressure, or very volatile liquids, which become very dense above their critical temperature and pressure. Their properties are between those of a gas and liquid, resulting in increasing ability to dissolve compounds. Their relatively high density, close to the density of liquids and, simultaneously, high diffusivity and low viscosity similar to the ones of gases, allow them to extract compounds faster than conventional liquid solvents. Additionally their solvating power can be easily adjusted by changing temperature and pressure, which makes them particularly suitable for selective fractionation of extracts.

The extraction of target solutes from liquid feedstocks using supercritical fluid extraction is accomplished in a column which promotes de contact between the supercritical fluids and the liquid matrix. The liquid mixture is continuously fed to the top of the column by a pump and the supercritical fluid is fed at the bottom of the column by a compressor. The supercritical fluid and the extracted solutes recovered from the liquid feed leave the column by an outlet at the top. The solutes are recovered in a cyclone by expansion of the supercritical fluid down to 6 MPa; the supercritical fluid is recompressed and reused again in the column. The pressure inside the column is controlled by a pneumatic valve located before the cyclone. This supercritical extraction column can be fed directly with vegetation waters but it can also operate with extracts previously obtained by extraction with biocompatible solvents, such as water, ethanol or mixtures of these solvents.

In the present invention the supercritical extraction step is accomplished in a temperature range between 30° C. and 200° C., preferentially between 30° C. and 80° C., at pressures ranging from 6 MPa and 40 MPa, preferentially between 8 MPa and 20 MPa.

Any fluid or mixture of fluids in the supercritical state or in the liquid sub-critical state can be used to perform the process described by this patent. Preferentially, the compressed fluid or mixture of fluids must be very volatile or be in the gas state at atmospheric conditions, in order to render easy its recover by expansion and/or evaporation after completion of the extraction step. For safety reasons the compressed fluid, or the mixture of these fluids, should be non-toxic and non-flammable and it must be recyclable for further use.

Nanofiltration and reverse osmosis are membrane separation techniques for processing of liquid streams, where the driving force for transport is the effective pressure difference between the feed (also retentate) and the permeate compartments. A correct selection of the nanofiltration and the reverse osmosis membranes, and the operating conditions of the related equipment, allows for obtaining a selective transport of the target solute(s) and relevant permeating flux(es).

The nanofiltration and reverse osmosis units include a feed vessel which contains the solution with the solutes to be recovered. The content of the feed vessel is delivered by a centrifugal pump or by a positive displacement pump to the nanofiltration or the reverse osmosis module(s) that comprise(s) a feed/retentate compartment, the selected membrane through which the target solute(s) permeate, and a permeate compartment. The permeate can be removed continuously or intermittently. After contacting the membrane, the retentate stream may be recycled to the feed vessel.

The feedstock stream consists on an aqueous or an hydroalcoholic solution. This solution may be vegetation water or extract obtained during the processing of olive residues. The target solutes to be recovered comprise all type of bioactive solutes.

The feedstock stream must be, preferentially, at a temperature below 150° C. if polymeric membranes are employed but it may be processed at a higher temperature if temperature-stable membranes, such as ceramic or metallic membranes, are used.

The nanofiltration and reverse osmosis membranes must act as a selective barrier, in order to avoid permeation of undesirable components from the feedstock, allowing permeation of the solute(s) with a desirable bioactivity. The membranes must have characteristics that lead to a high flux of the target solute(s) and low or zero flux of the undesirable components of the feedstock.

The membrane may be polymeric or inorganic. They may also comprise both polymeric and inorganic materials. In what concerns their structure they may also be homogeneous or composites; in the later case they may include different layers constituted by different materials and/or with different morphological characteristics. Each one of those layers may have a different thickness.

Concerning their chemical nature the membranes may present a hydrophobic character, meaning that they are more permeable to hydrophobic chemical species, i.e., to chemical species that present an infinite activity coefficient higher than unity in aqueous solution. The membranes may also present a hydrophilic character, which means that they are more permeable to water than to organic compounds.

The membranes may have a flat or a tubular geometry and they may be arranged in a plate-and-frame module, in a spiral-wound module, in a hollow fibre module, in a capillary module or in a tubular module.

The feedstock stream may be fed in a continuous, semi-continuous or batch mode. The membrane module(s) may be submerged in one or more feedstock vessels, or placed externally to the feedstock vessel. In case that more than one membrane module is used, they may be arranged in series or in parallel.

To establish the driving force needed to promote the transport of solute(s) through the membrane, a pressure difference is established between the two compartments (feed/retentate and permeate) of membrane module(s). The value of absolute pressure difference should be in the range of 0.5 MPa to 3.0 MPa, preferentially, in the range of 1.0 MPa to 1.5 MPa for the nanofiltration operation; in the reverse osmosis operation the range of absolute pressure difference stays between 3 MPa and 8 MPa, preferentially in the range of 4 MPa to 6 MPa.

The natural hydroxytyrosol-rich concentrate (streams G and L in FIG. 2) obtained by the process of the present invention contains a minimum mass fraction of 15% in hydroxytyrosol and maximum mass fraction of 98% of this compound. The selection of the operating conditions and of the characteristics of the nanofiltration membrane, such as its molecular weight cut-off, allows to selectively permeate the bioactive compounds with desired properties, while assuring the retention of compounds with higher molecular weight, which may exhibit a detrimental biological activity. Aiming this selective fractionation of bioactive compounds present in the feed stream, the molecular weight cut-off of the nanofiltration membrane should be below 1000 Da, preferentially below 400 Da, most preferentially below 300 Da. The value of the molecular weight cut-off of nanofiltration membranes is calculated by determining the rejection of reference solutes, such as glucose or saccharose, from aqueous solutions.

The concentrated extracts contain other bioactive compounds beside hydroxytyrosol, originally present in the olive fruit of leafs, according to the starting material used. The concomitant presence of hydroxytyrosol and other desired bioactive compounds, which results from the process of the present invention, originates a synergy between them that reflects on the overall biological activity of the concentrated extracts. As a consequence, these hydroxytyrosol-rich concentrates exhibits anti-oxidant, anti-microbial, anti-inflammatory and anti-carcinogenic activities, which are superior to the activities observed for isolated hydroxytyrosol in equivalent concentration.

The hydroxytyrosol-rich concentrate can be prepared in the form of a liquid, a solid or an emulsion. The liquid form refers to an aqueous solution, which may be evaporated, lyophilised or atomised in order to produce solid particles. Additionally, different specific formulations may be prepared using bio-compatible excipients and lipidic matrixes, in order to protect the bioactivity of the recovered compounds.

Alternatively, the hydroxytyrosol-rich concentrate may be prepared in the form of an emulsion, in order to render easier its incorporation in different products. These emulsions may be prepared by using polyglycerol esters from fatty acids, glycerol esters from fatty acids, lecithin or combinations of these emulsifiers. These formulations should have a volume fraction between 5% and 60% in hydroxytyrosol, preferentially, between 30% and 55%. Citric acid may be added to these emulsions in order to stabilise them.

Applications of the hydroxytyrosol-rich concentrate in its various delivery forms include the food, pharmaceutical and cosmetics industries.

EXAMPLES

Aiming to illustrate the present invention, four examples on the use of this invention are given. These examples are not restrictive.

Example 1

Production of a polyphenolic-rich concentrate containing hydroxytyrosol through an integrated procedure comprising extraction with biocompatible solvents and subsequent fractionation by supercritical fluid extraction.

Figure 3:
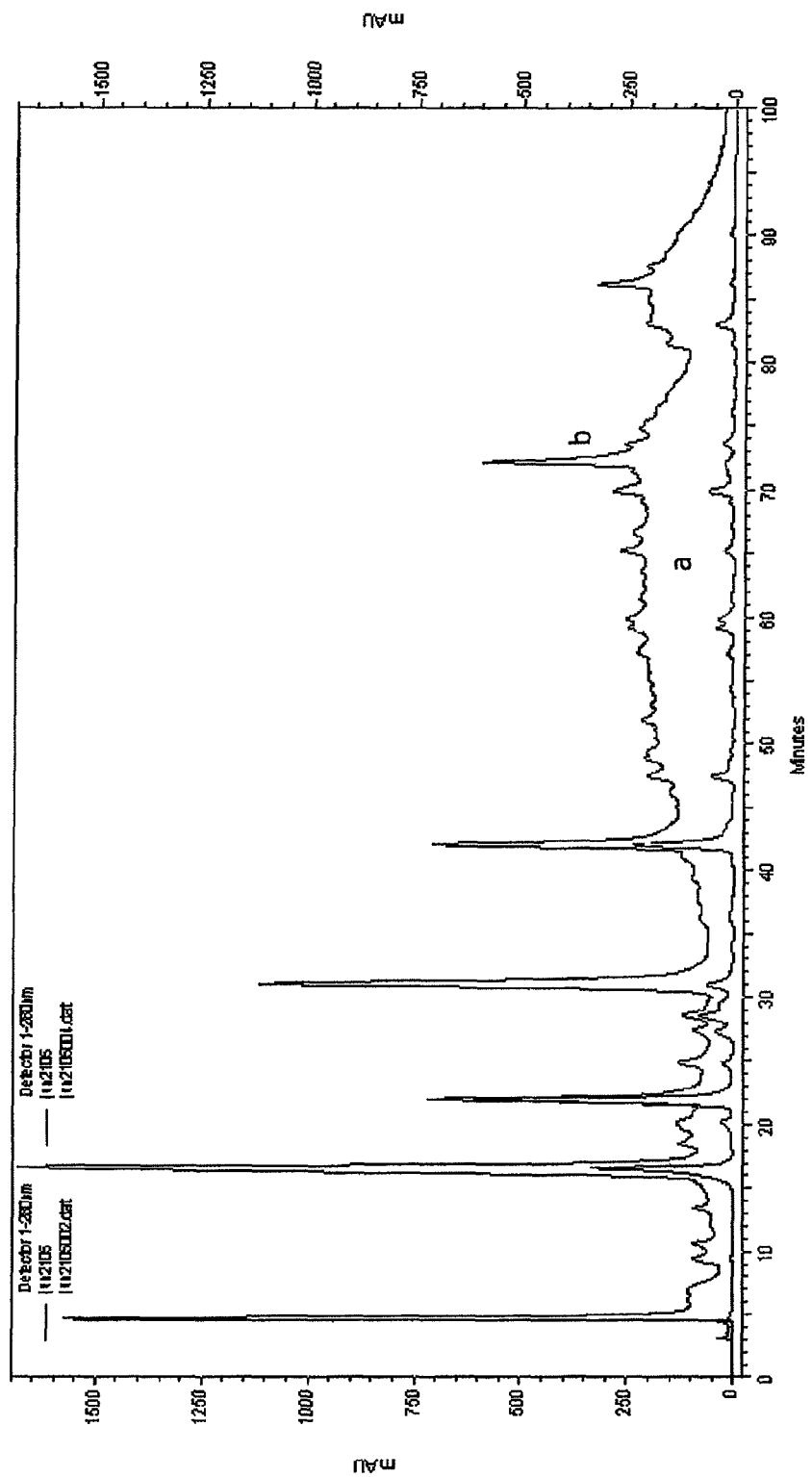
FIG. 3 shows the chromatograms obtained by liquid chromatography of: (a) a rich-concentrate obtained by supercritical extraction; (b) the corresponding feed solution. Beside hydroxytyrosol it is noticeable the presence among others, in the extract, of luteolin and hydroxycinamic acids, such as the cafeic acid and the p-coumaric acid.

300 g of semi-solid residue from a two-phase olive oil process were extracted with 900 ml of a hydroalcoholoc solution with a volume ratio of 90:10 (ethanol:water). The extract recovered was centrifuged and the supernatant was fed with a supercritical fluid extraction column with a structured packing supplied by Sulzer; the column was 4 m high, with an internal diameter of 4 cm. The liquid feed was extracted countercurrently with supercritical carbon dioxide. 500 ml of extract were recovered from the column. This extract was analysed by liquid chromatography and the corresponding chromatogram is presented in FIG. 3. This figure shows the chromatograms obtained for: (a) a rich-concentrate obtained by supercritical extraction; (b) the corresponding feed solution. It can be observed from FIG. 3 (a) that the peak corresponding to hydroxytyrosol and its derivatives represent 35% of the area of all peaks. Beside hydroxytyrosol it is noticeable the presence among others, in the extract, of luteolin and hydroxycinamic acids with high biological activity, such as the cafeic acid and the p-coumaric acid.

Example 2

Production of a polyphenolic-rich concentrate containing hydroxytyrosol using an integrated nanofiltration/revere osmosis procedure.

Figure 4:
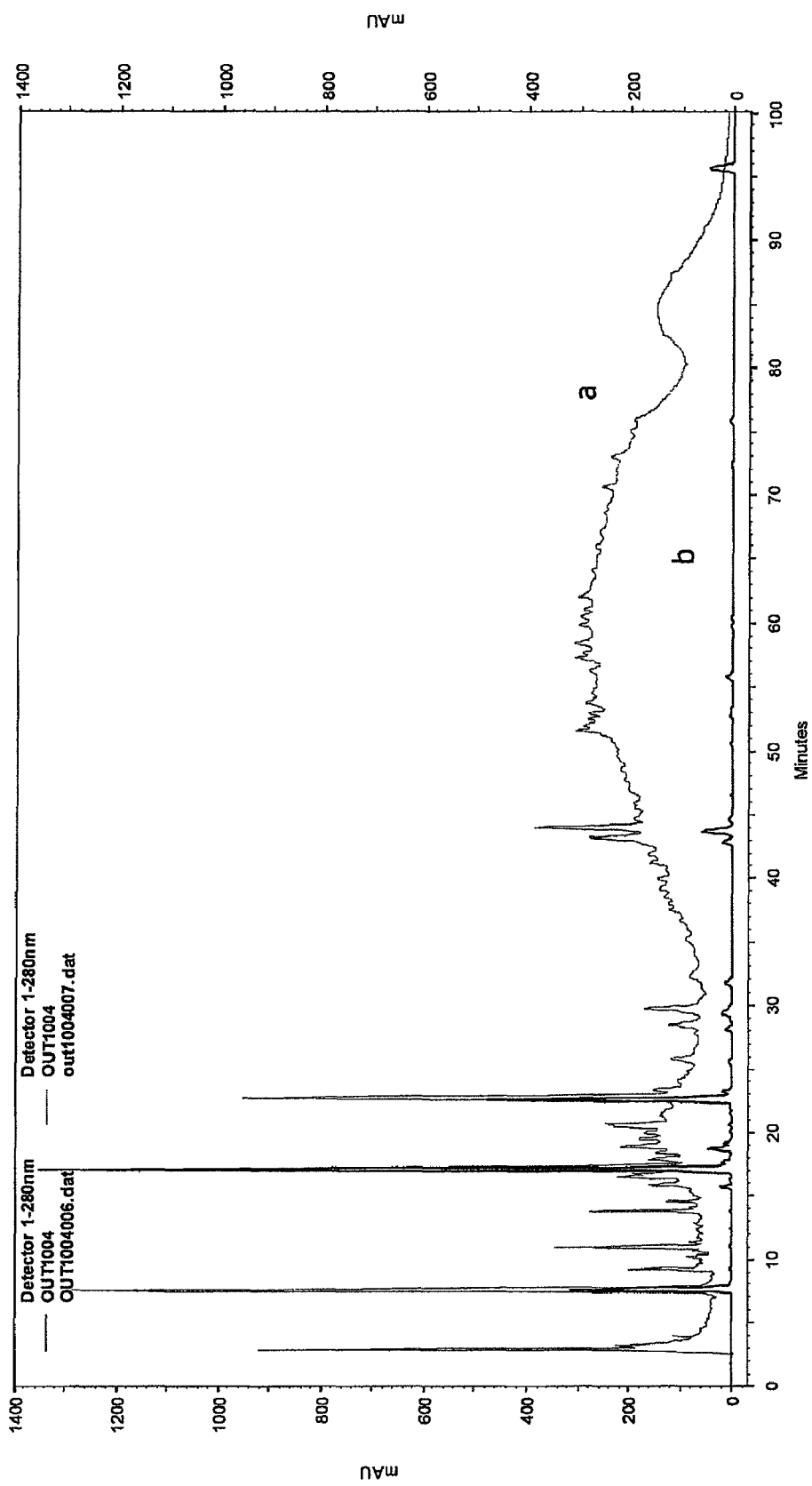
FIG. 4 shows a comparison between the chromatograms obtained by liquid chromatography of: (a) aqueous extract, obtained from leaching of an olive cake with water at ambient temperature, fed to the nanofiltration process (b) the concentrate stream obtained by nanofiltration/reverse osmosis. It is noticeable the increase of the concentration of hydroxytyrosol and tyrosol in the stream produced by nanofiltration/reverse osmosis.

250 ml of an aqueous extract, obtained from leaching of an olive cake with water at ambient temperature, was fed to a nanofiltration unit where it was processed at an absolute pressure difference of 1 MPa. 240 ml of permeate were obtained with a recovery yield of hydroxytyrosol of 70%. The permeate obtained was further processed by reverse osmosis operated at 2.5 MPa. The resulting retentate was characterised by liquid chromatography. FIG. 4 shows the chromatograms obtained for (a) aqueous extract fed to the nanofiltration process and (b) the concentrated retentate obtained after the nanofiltration/reverse osmosis procedure described. It is noticeable the increase of the concentration of hydroxytyrosol and tyrosol in the stream produced by nanofiltration/reverse osmosis. The nanofiltation membrane was a Desal DK, from General Electric, with a molecular weight cut-off of 250 Da. The reverse osmosis membrane was a Filmtec SW 30 from Dow.

Example 3

Characterization of the anti-microbial activity of a hydroxytyrosol-rich concentrated extract, produced by nanofiltration/reverse osmosis.

Figure 5:
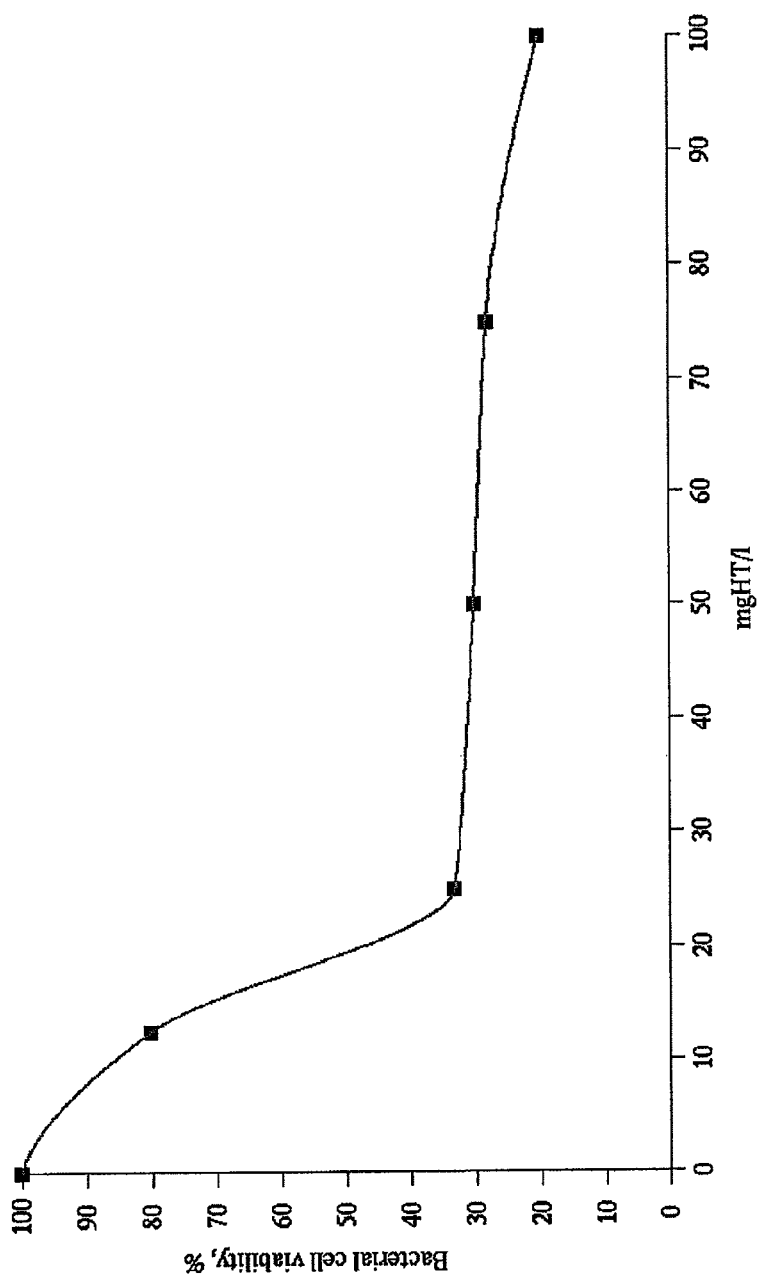
FIG. 5 shows the anti-bacterial effect of the hydroxytyrosol-rich extract obtained by integrated nanofiltration/reverse osmosis. The bacteria culture was of *Ehrlichia ruminantum*.

The anti-microbial activity of a hydroxytyrosol-rich concentrated extract obtained by integrated nanofiltration/reverse osmosis was evaluated by adding different concentrations of this extract to animal cell cultures infected with the bacteria *Ehrlichia ruminantum*. FIG. 5 shows that the percentage of dead bacterial cells raises up to 80% after exposure to the extract.

Example 4

Characterization of the anti-cancer activity of a hydroxytyrosol-rich concentrated extract, produced by nanofiltration/reverse osmosis.

Figure 6:
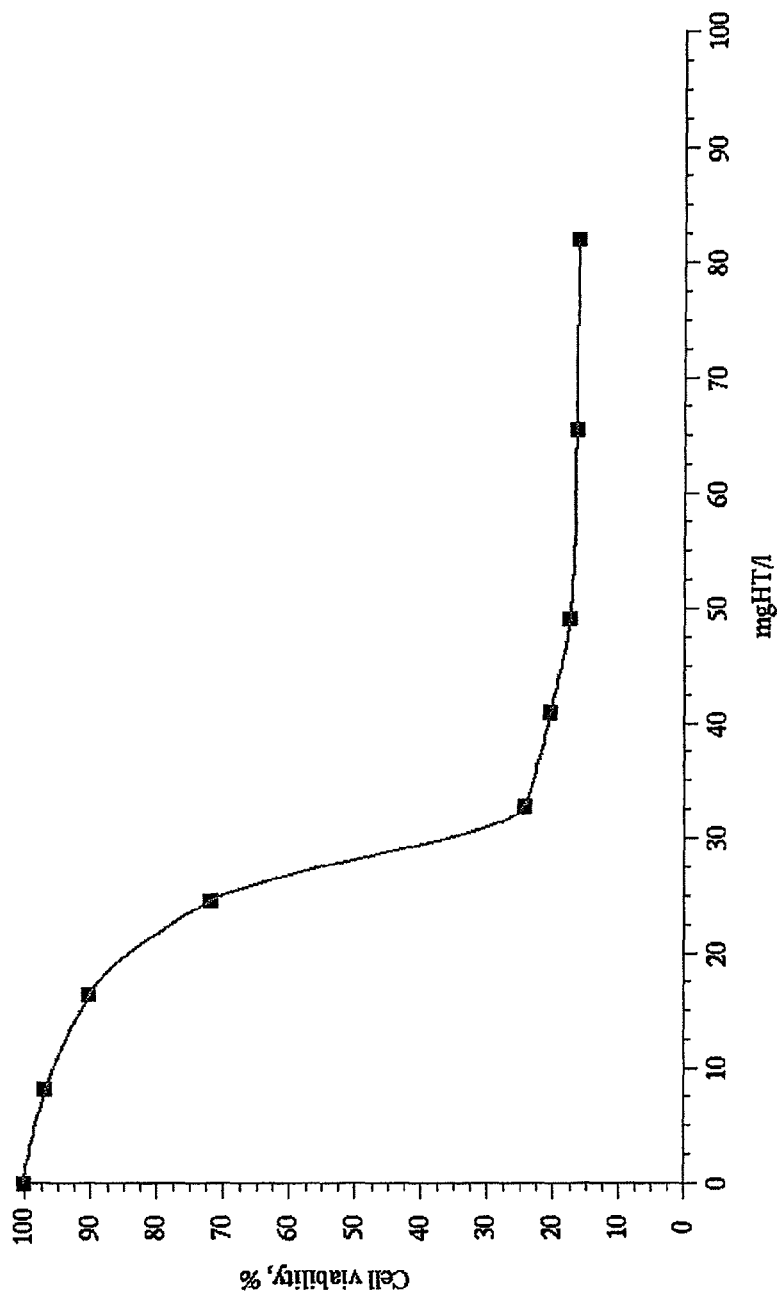
FIG. 6 shows the effect of the hydroxytyrosol-rich extract obtained by integrated nanofiltration/reverse osmosis as an agent able to reduce the proliferation of cancer cells. The cells used in this example are from the cell line HT 29 (human colonic adenocarcinoma cells).

The anti-cancer activity of a hydroxytyrosol-rich concentrated extract obtained by integrated nanofiltration/reverse osmosis was evaluated by adding different concentrations of this extract to a culture of human colonic adenocarcinoma cells (cell line HT 29). FIG. 6 shows that the percentage of viable cancer cells decreases to less than 20% after exposure to the extract.

REFERENCES

| Patents | |
| --- | --- |
| U.S. Pat. No. 6,361,803 | Cuomo et al. |
| U.S. Pat. No. 6,849,770 | Fernandez-Bolanos et al. |
| U.S. Pat. No. 5,714,150 | Nashman |
| WO 0218310 | Crea |
| EP 1 623 960 A1 | Villanova et al. |

OTHER REFERENCES

Allouche et al. "Toward a High Yield Recovery of Antioxidants and Purified Hydroxytyrosol from Olive Mill Wastewaters", J. Agric. Food Chem. 52(2) (2004) 267-273

Ryan et al. "Recovery of phenolic compounds from Olea europaea" Anal. Chim. Acta 445 (2001) 67-77

DellaGreca et al. "Low-molecular-weight components of olive oil mill waste-waters", Phytochem. Anal. 15 (2004) 184-188

DellaGreca et al. "Phytotoxicity of low-molecular-weight phenols from olive mill waste waters", Bull. Environ. Contam. Toxicol. 67 (2001) 352-359

Drouiche et al. "A compact process for the treatment of olive mill wastewater by combining UF and UV/H2O2 techniques", Desalination 169 (2004) 81-88

Fernandez-Bolanos et al. "Production in Large Quantities of Highly Purified Hydroxytyrosol from Liquid-Solid Waste of Two-Phase Olive Oil Processing or Alperujo", J. Agric. Food Chem. 50 (2002) 6804-6811

Fernandez-Bolanos et al. "Total Recovery of the Waste of Two-Phase Olive Oil Processing: Isolation of Added-Value Compounds", J. Agric. Food Chem. 52 (2004) 5849-5855

Lesage-Meessen et al. "Simple phenolic content in olive oil residues as a function of extraction systems", Food Chemistry 75 (2001) 501-507

Marrugat et al. "Effects of differing phenolic content in dietary olive oils on lipids and LDL oxidation. A randomized controlled trial", Eur J Nutr. 43 (2004) 140-147

Manna et al. "Transport mechanism and metabolism of olive oil hydroxytyrosol in Caco-2 cells", FEBS Lett. 470 (2000) 341-344

Mullinacci et al. "Polyphenolic content in olive oil wastewaters and related olive samples", J. Agric. Food Chem. 49 (2001) 3509-3514

Obied et al. "Bioactivity and Analysis of Biophenols Recovered from Olive Mill Waste", J. Agric. Food Chem. (Review) 53 (2005) 823-837

Quiles et al. "Olive oil phenolics: effects on DNA oxidation and redox enzyme mRNA in prostate cells", British Journal of Nutrition 88 (2002) 225-234

Bouzid et al. "Fungal enzymes as a powerful tool to release simple phenolic compounds from olive oil by-product", Process Biochemistry 40 (2005) 1855-1862

Owen et al. "Olive oil consumption and health: the possible role of antioxidants", Lancet Oncol. 1 (2000) 107-112

Rodis et al. "Partitioning of olive oil antioxidants between oil and water phases", J. Agric. Food Chem. 50 (2002) 596-601

Schieber et al. "By-products of plant food processing as a source of functional compounds recent developments", Trends in Food Science & Technology 12 (2001) 401-413

Tuck et al. "Major phenolic compounds in olive oil: metabolism and health effects", Journal of Nutritional Biochemistry 13 (2002) 636-644

Turano et al. "An integrated centrifugation-ultrafiltration system in the treatment of olive mill wastewater", J. Membr. Sci. 209 (2002) 519-531

Visioli et al. "Antioxidant and other biological activities of olive mill wastewaters", J. Agric Food Chem. 47 (1999) 3397-3401

Visioli et al. "Olive oil phenolics are dose dependently absorbed in humans", FEBS Letters 468 (2000) 159-160

Visioli et al. "Antioxidant and other biological activities of phenols from olives and olive oil", Medicinal Research Reviews 22 (2002) 65-75

Visioli et al. "Biological activities and metabolic fate of olive oil phenols", Eur. J. Lipid Sci. Technol. 104 (2002) 677-684

The invention claimed is:

1. A method of obtaining a hydroxytyrosol-rich concentrate from olive tree residues and sub-products using clean technologies consisting essentially of:
   supplying a flow stream containing hydroxytyrosol and other bioactive compounds to a nanofiltration unit with a molecular weight cut-off lower than 300 Da,
      wherein said hydroxytyrosol and other bioactive compounds are recovered in a permeate stream from a permeate compartment of said nanofiltration unit, and
   followed by supplying the permeate stream from said nanofiltration unit to a feed compartment of a reverse osmosis unit,
      wherein said hydroxytyrosol and other bioactive compounds are retained and concentrated in a retentate stream, and
      wherein the transport of solvents and solutes in both said nanofiltration unit and said reverse osmosis unit is driven by a pressure gradient between said feed compartment and said permeate compartment.

2. The method as claimed in claim 1, wherein the bioactive compounds present in the flow stream supplied to the nanofiltration unit comprise at least hydroxytyrosol, luteolin and hydroxycinnamic acids.

3. The method as claimed in claim 1, wherein the bioactive compounds retained and concentrated in the retentate stream of the reverse osmosis unit comprise at least hydroxytyrosol, luteolin and hydroxycinnamic acids.

4. The method as claimed in claim 1, wherein the olive tree residues and sub-products are a feedstock comprising vegetation waters, solid or semi-solid residues resulting from olive oil production, and other sub-products from the olive tree.

5. The method as claimed in claim 4, wherein said solid or semisolid residues and sub-products are processed by extraction at ambient temperature with biocompatible solvents prior to processing by nanofiltration.

6. The method as claimed in claim 1, wherein the nanofiltration unit is fed with a liquid feedstock which consists of vegetation waters or of aqueous, alcoholic or hydroalcoholic liquid extracts obtained by processing said olive tree residues and said sub-products.

7. The method as claimed in claim 6, wherein the nanofiltration unit is operated at an absolute pressure difference between the feed compartment and the permeate compartment in the range of 0.5 MPa to 3.0 MPa and wherein the reverse osmosis unit is operated at an absolute pressure difference in the range of 3 MPa to 8 MPa.

8. The method as claimed in claim 1, wherein the nanofiltration unit and reverse osmosis unit comprise a nanofiltration membrane and a reverse osmosis membrane, respectively, wherein the nanofiltration membrane and the reverse osmosis membrane are homogeneous or composites, polymeric or inorganic or comprising both polymeric and inorganic materials.

9. The method as claimed in claim 8, wherein the nanofiltration membrane and the reverse osmosis membrane have a flat geometry or a tubular geometry, being arranged in a plate-and-frame module, in a spiral-wound module, in a hollow fibre module, in a capillary module or in a tubular module.

10. The method as claimed in claim 9, wherein one or more modules are arranged in series or in parallel.

11. The method as claimed in claim 10, wherein at least one of the nanofiltration unit and the reverse osmosis unit contains one or more membrane modules.

12. The method as claimed in claim 1, wherein at least one of the nanofiltration unit and the reverse osmosis unit has independently controllable environments with controllable parameters.

13. The method as claimed in claim 12, wherein the controllable parameters of at least one of the nanofiltration unit and the reverse osmosis unit are the temperature, the pressure and the pH.

14. The method as claimed in claim 6, wherein the liquid feedstock is fed to the nanofiltration unit in a continuous, semi-continuous or batch mode.

15. The method as claimed in claim 4, wherein said other sub-products from the olive tree comprise olive stones and olive leaves.

16. The method as claimed in claim 5, wherein said biocompatible solvents comprise water, ethanol or a mixture of both these solvents.

17. The method as claimed in claim 2, wherein the bioactive compounds present in the flow stream supplied to the nanofiltration unit further comprise at least caffeic acid and p-coumaric acid.

18. The method as claimed in claim 3, wherein the hydroxycinnamic acids are at least one of caffeic acid and p-coumaric acid.

19. The method as claimed in claim 7, wherein the nanofiltration unit is operated at an absolute pressure difference in the range of 1.0 MPa to 1.5 MPa.

20. The method as claimed in claim 7, wherein the reverse osmosis unit is operated at an absolute pressure difference in the range of 4 MPa to 6 MPa.

* * * * *